United States Patent [19]

Winston et al.

[11] Patent Number: 5,723,003
[45] Date of Patent: Mar. 3, 1998

[54] EXPANDABLE GRAFT ASSEMBLY AND METHOD OF USE

[75] Inventors: Thomas R. Winston, Leawood; John Neet, Lawrence, both of Kans.

[73] Assignee: Ultrasonic Sensing and Monitoring Systems, Kansas City, Mo.

[21] Appl. No.: 585,470

[22] Filed: Jan. 16, 1996

Related U.S. Application Data

[63] Continuation of Ser. No. 305,060, Sep. 13, 1994, abandoned.

[51] Int. Cl.⁶ ............................................. A61F 2/04
[52] U.S. Cl. .................. 623/1; 623/12; 606/194; 606/195
[58] Field of Search ................... 623/1, 12; 606/191, 606/192, 194, 195, 108

[56] References Cited

U.S. PATENT DOCUMENTS

| | | | |
|---|---|---|---|
| 4,140,126 | 2/1979 | Choudhury . | |
| 4,503,569 | 3/1985 | Dotter | 604/195 |
| 4,665,918 | 5/1987 | Garza et al. . | |
| 4,733,665 | 3/1988 | Palmaz . | |
| 4,763,653 | 8/1988 | Rockey . | |
| 4,877,030 | 10/1989 | Beck et al. | 623/1 |
| 4,969,458 | 11/1990 | Wiktor . | |
| 4,994,071 | 2/1991 | Macgregor . | |
| 5,007,926 | 4/1991 | Derbyshire . | |
| 5,019,085 | 5/1991 | Hillstead . | |
| 5,026,377 | 6/1991 | Burton et al. . | |
| 5,041,126 | 8/1991 | Gianturco . | |
| 5,078,720 | 1/1992 | Burton et al. . | |
| 5,078,726 | 1/1992 | Kreamer . | |
| 5,100,429 | 3/1992 | Sinofsky et al. . | |
| 5,108,417 | 4/1992 | Sawyer . | |
| 5,122,154 | 6/1992 | Rhodes | 623/12 |
| 5,123,917 | 6/1992 | Lee . | |
| 5,135,536 | 8/1992 | Hillstead | 623/12 |
| 5,147,370 | 9/1992 | McNamara et al. . | |
| 5,151,105 | 9/1992 | Kwan-Gett . | |
| 5,211,654 | 5/1993 | Kaltenbach | 606/191 |
| 5,236,447 | 8/1993 | Kubo et al. | 623/12 |
| 5,258,027 | 11/1993 | Berghaus | 623/12 |
| 5,306,294 | 4/1994 | Winston et al. . | |
| 5,316,023 | 5/1994 | Palmaz et al. | 623/12 |
| 5,330,500 | 7/1994 | Song | 623/1 |
| 5,366,473 | 11/1994 | Winston et al. | 623/12 |
| 5,405,379 | 4/1995 | Lane . | |
| 5,443,500 | 8/1995 | Sigwart . | |

OTHER PUBLICATIONS

PCT Publication No. WO 91/17789 28 Nov. 1991.
PCT Publication No. WO 91/15254 17 Oct. 1991.
PCT Publication No. WO 82/0333 14 Oct. 1982.
CCCP No. 694197 30 Oct. 1979.

*Primary Examiner*—John G. Weiss
*Assistant Examiner*—Bruce E. Snow

[57] ABSTRACT

A graft assembly is provided for placement in a body passage having a generally tubular inner wall of predetermined diameter. The graft assembly includes an elongated outer tubular graft presenting inner and outer graft surfaces, and first and second outer stents secured to the graft. The first outer stent has expanded and contracted conditions and possesses a spring force that urges the first outer stent toward the expanded condition. When in the expanded condition, the first stent presents an outer diameter greater than the predetermined diameter of the inner wall of the body passage. The second outer stent also has expanded and contracted conditions and possesses a spring force that urges the second outer stent toward the expanded condition. However, the second outer stent, in the expanded condition, presents an outer diameter substantially equal to the predetermined diameter of the inner wall of the body passage so that the second outer stent supports the graft at the position spaced from the first outer stent.

11 Claims, 4 Drawing Sheets

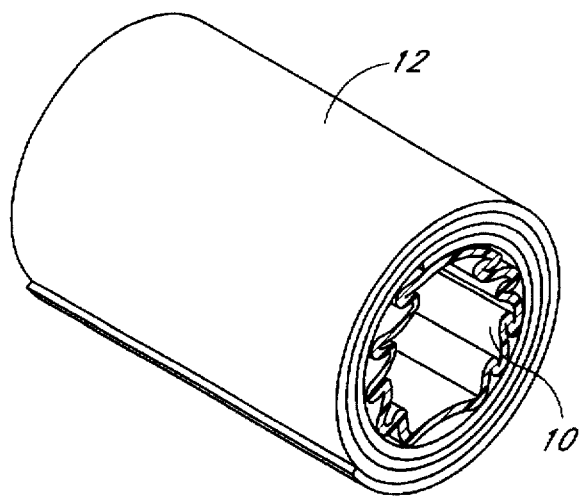
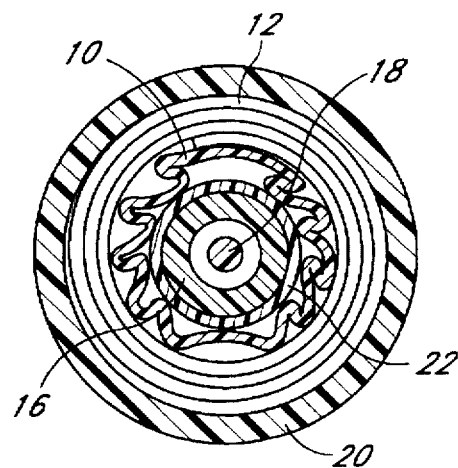
FIG.1  FIG.2
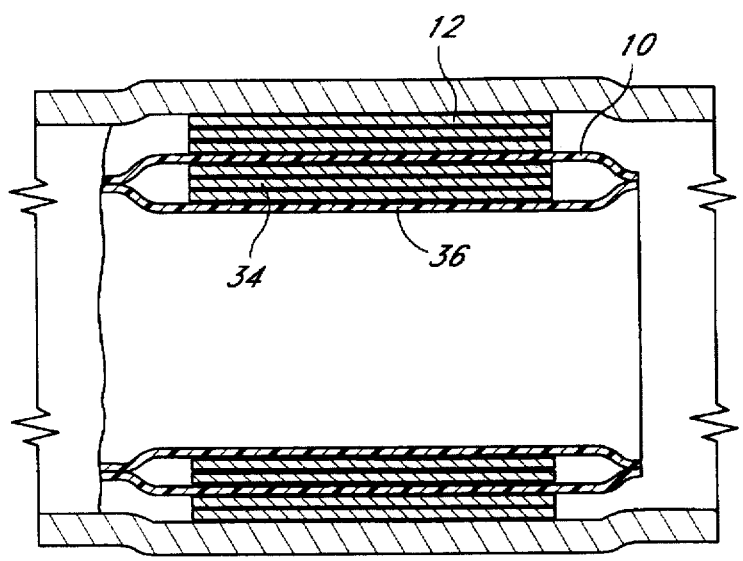
FIG.3

EXPANDABLE GRAFT ASSEMBLY AND METHOD OF USE

This application is a File Wrapper Continuation of application Ser. No. 08/305,060, filed 13 Sep. 1994 now abandon.

BACKGROUND OF THE INVENTION

1. Field of the Invention

The present invention relates generally to the field of medical implants, and more particularly to a graft for placement in a body passage to reinforce or bypass a damaged area.

2. Discussion of the Prior Art

Tubular prostheses commonly known as stents have been used to reinforce and strengthen damaged blood vessels and other body passages. For example, the blood vessels can collapse, dilate, become partially occluded or otherwise damaged by disease or other causes. The presence of an aneurysm or stricture in the blood vessel often requires implantation of a stent to strengthen the vascular wall in the area of the damage. Other passages in the body can also sometimes benefit from stent implantation, including the esophagus, the trachea, the gastro-intestinal tract, the bile duct, the ureter, the urethra or essentially any tubular structure in the body.

The benefits of self-expanding stents have been recognized. A self-expanding stent is held in a contracted state until it has been positioned properly, typically with the aid of an instrument such as a catheter. After the stent has been placed properly in the damaged blood vessel, it is allowed to expand against the damaged vessel wall in order to reinforce the damaged area. An example of a self-expanding stent construction is disclosed in U.S. Pat. No. 5,306,294, issued 26 Apr. 1994 to Winston et al., and entitled Stent Construction of Rolled Configuration. The disclosure of this patent is hereby incorporated in the present application by this express reference.

It is also conventional to provide an expandable intraluminal vascular graft formed of a graft material on which a plurality of separate scaffold members are mounted. The scaffold members provide circumferential rigidity to the graft, and are expandable so that the graft may be positioned within the body lumen and then expanded radially outward to the size of the lumen. The scaffold members are formed of a material that is deformed during expansion of the scaffold members so that the members remain in the expanded condition and do not return to the original contracted diameter.

A problem encountered in the use of conventional grafts resides in the possibility of such grafts to continually expand and form graft aneurysms when there is no suitable body wall within which the graft is positioned. Further, conventional grafts are difficult to place because of the lack of any means for retaining the graft in place within the passage until after deformation of the graft or scaffold members.

OBJECTS AND SUMMARY OF THE INVENTION

Accordingly, it is an object of the present invention to provide a graft assembly including a self-adjusting means for maintaining a graft in place within a body passage in order to simplify initial placement of the graft, and to accommodate expansion of the body passage.

It is another object of the present invention to provide an assembly for supporting a graft during placement in the body passage, and for deploying the graft once properly positioned within the passage. By achieving this object, installation of the graft is simplified, allowing use of the graft both intraluminally and as a bypass around a damaged section of the passage.

In accordance with these and other objects evident from the following description of a preferred embodiment, a graft assembly constructed in accordance with the present invention includes an elongated tubular graft presenting inner and outer graft surfaces, and first and second types of stents. The first type of stent is formed of a flexible sheet arranged in a multiple layer roll having expanded and contracted conditions, and possesses a spring force that urges the roll toward the expanded condition. The first stent, when in the expanded condition, presents an outer diameter greater than the diameter of the inner wall of the body passage, and holds the graft in place.

The second type of stent also includes a flexible sheet arranged in a multiple layer roll having expanded and contracted conditions, and possesses a spring force that urges the roll toward the expanded condition. However, the roll of each second type of stent, when in the expanded condition, presents an outer diameter substantially equal to the diameter of the desired position of the graft and shapes the graft even if there is no body wall present. This construction prevents the aneurysmal formation or over distention of the graft along its length, and can also provide support in other areas such as those in which there might normally be a concern of kinking of the graft.

The assembly for use in placing the graft in the body passage includes a core, and a retaining means for retaining the stents in the contracted condition on the core while the core is being inserted into the passage. The retaining means is shiftable for releasing the stents to move against the inner wall of the passage toward the expanded condition.

By providing a graft constructed in accordance with the present invention, numerous advantages are realized. For example, by providing two types of stents on the graft, one type which is continually biased toward a further expanded condition, and another type which reaches the expanded condition and shapes the graft while preventing it from expanding too far, the graft is retained in position within the body passage, and is supported along the entire length of the graft.

BRIEF DESCRIPTION OF THE DRAWING FIGURES

A preferred embodiment of the present invention is described in detail below with reference to the attached drawing figures, wherein:

FIG. 1 is a fragmentary perspective view of a graft assembly constructed in accordance with the preferred embodiment, illustrating a first type of stent of the assembly in a contracted condition;

FIG. 2 is a cross-sectional view of the graft assembly, illustrating the graft supported on an installation assembly used to place the graft assembly in a body passage;

FIG. 3 is a fragmentary sectional view of an end of the graft assembly, illustrating the completed assembly in position within the body passage;

DETAILED DESCRIPTION OF THE PREFERRED EMBODIMENT

Figure 4:
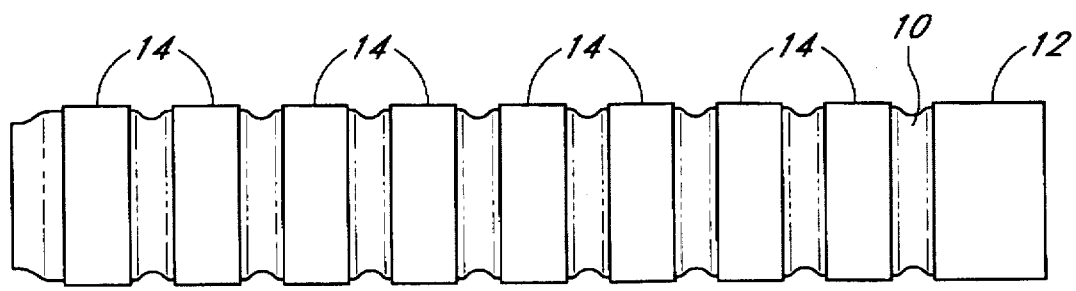
FIG. 4 is a top plan view of a first preferred construction of the graft assembly.

A graft assembly constructed in accordance with a preferred embodiment of the present invention is illustrated in FIG. 4, and broadly includes an elongated tubular graft 10, one or more of a first type of stent 12 for holding the stent in place within a body passage, and a plurality of a second type of stent 14 for shaping the graft and preventing it from expanding beyond a desired diameter.

The first type of stent 12 is shown in FIG. 1, and is formed of an initially flat flexible metal sheet arranged in a multiple layer roll having expanded and contracted conditions. The expanded condition of the stent is illustrated in FIGS. 3, 7, 9 and 10, while the contracted condition is shown in FIGS. 1, 2, 6 and 8. The first type of stent 12 is preferably constructed of a stainless steel foil which is commercially available under the trade designation pH15-9 Condition CH900, having a thickness in an exemplary construction of 0.0127 millimeters. However, any other suitable material may be used.

When the roll is arranged in the contracted condition, it is in the shape of a spiral roll presenting an outside diameter of about 2-5millimeters. This size may vary, and is designed to enable placement of the graft in the body passage. The sheet is long enough in the circumferential direction of the roll that there are several layers of the sheet which overlap one another when the roll is in either the contracted or expanded condition.

The sheet produces an inherent spring force which urges the roll toward the expanded condition. For example, the sheet may initially be rolled to a diameter of about 10-25 millimeters or other desired diameter, and then heat treated in that condition to relax the internal stresses that are induced by winding the sheet to this coiled condition. Following heat treatment, the material can then be rolled into a tighter coil having an outer diameter of, e.g. 2-5 millimeters or other desired diameter so that the internal spring force of the roll urges it to unwind toward the original diameter in the expanded condition of the roll. The expanded diameter of the stent 12 is designed to be slightly larger than the diameter of the body passage, and the construction of the stent may vary depending upon the size of passage in which the graft is to be placed.

Figure 8:
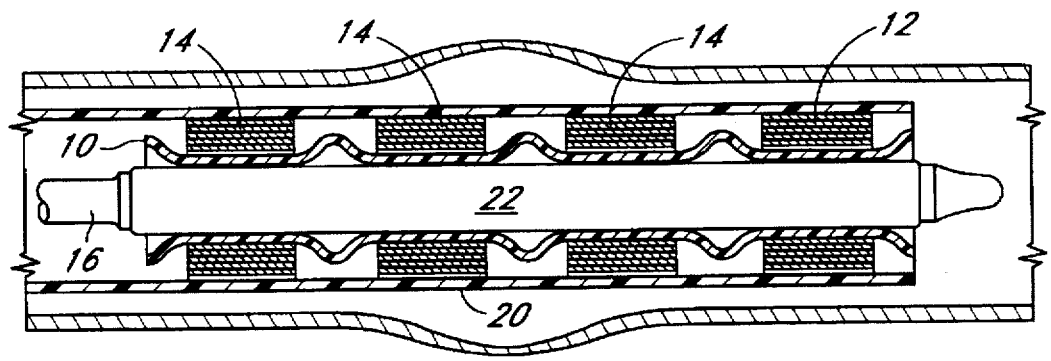
FIG. 8 is a sectional view of the body passage, illustrating an initial step of installation of the stent assembly of FIG. 6.
Figure 9:
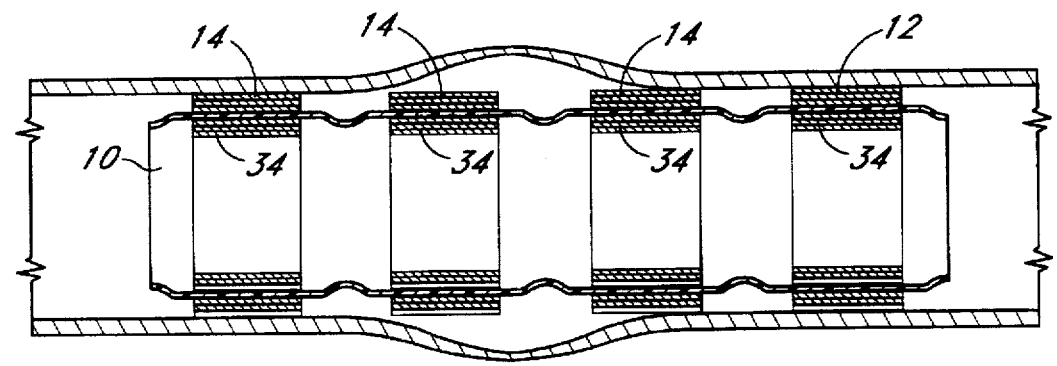
FIG. 9 is a sectional view of the body passage, illustrating an intermediate condition of the graft assembly.
Figure 10:
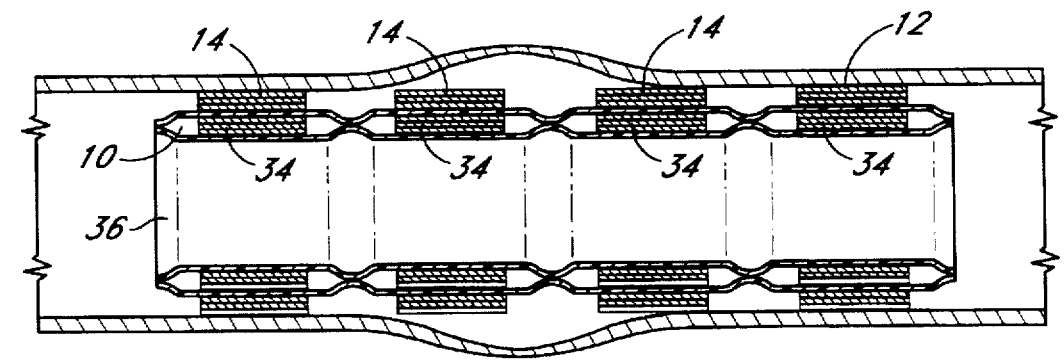
FIG. 10 is a sectional view of the body passage, illustrating the completed graft assembly.

The plurality of second stents 14 are each formed of an initially flat flexible metal sheet arranged in a multiple layer roll having expanded and contracted conditions. The expanded condition of the stents is illustrated in FIGS. 9 and 10, while the contracted condition is shown in FIG. 8. The second stents are preferably constructed of a stainless steel foil which is commercially available under the trade designation pH15-9 Condition CH900, having a thickness in an exemplary construction of 0.0127 millimeters. However, any other suitable material may be used.

When the roll of each second stent is arranged in the contracted condition, it is in the shape of a spiral roll presenting an outside diameter of about 2-5 millimeters. This size may vary, and is designed to enable placement of the graft in the body passage. The sheet is long enough in the circumferential direction of the roll that there are several layers of the sheet which overlap one another when the roll is in either the contracted or expanded condition.

The sheet produces an inherent spring force which urges the roll toward the expanded condition, wherein the shape of a spiral roll presents an outside diameter adapted to be substantially equal to the desired diameter of the passage, and smaller than the expanded sized of the first stents.

The roll of each second stent 14 is preferably initially rolled to the desired expanded diameter, and then heat treated in that condition to relax the internal stresses that are induced by winding the roll to this condition. Following heat treatment, the material can then be rolled into a tighter roll having an outer diameter of, e.g. 2-5 millimeters or other suitable diameter, so that the stent may be inserted into the body passage. Each of the second stents are spaced longitudinally from adjacent stents so that circumferential support of the graft is provided along substantially the entire length thereof.

Figure 6:
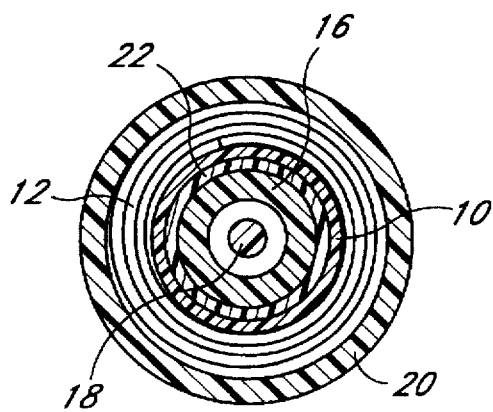
FIG. 6 is a cross-sectional view of a graft assembly constructed in accordance with another preferred construction incorporating an alternate graft material.
Figure 7:
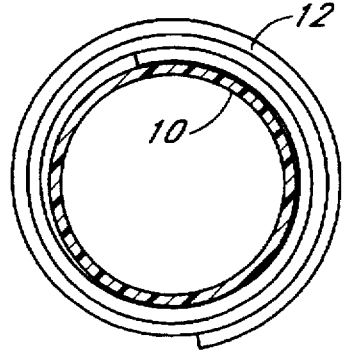
FIG. 7 is a cross-sectional view of the graft assembly of FIG. 6, illustrating the assembly in an expanded condition.

The graft material used in the graft 10 may be formed of any suitable prosthesis material such as polytetrafluoroethylene (pTFE) or the like, and may take either of two forms. As shown in FIGS. 1 and 2, the graft may be sized to correspond to the diameter of the inner wall of the passage such that the graft material is held loosely by the stents 12, 14 in the contracted condition and unfolds when the stents are in their expanded condition. Alternately, as shown in FIGS. 6 and 7, the graft material may be formed of a diameter corresponding to the contracted condition of the stents such that the graft material is adapted to be deformed and expanded to the size of the expanded stents upon placement of the graft in the body passage.

Figure 5:
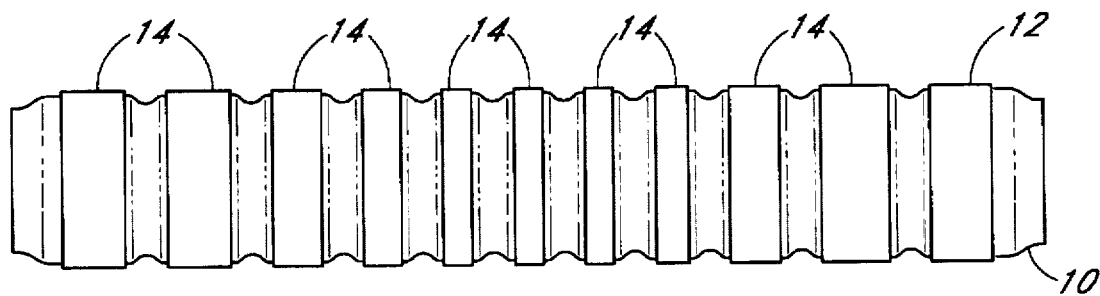
FIG. 5 is a top plan view of a graft assembly constructed in accordance with another preferred construction.

The stents 12, 14 may secured to the graft 10 in any desired manner, such as by mechanical fastening or chemical bonding or welding. Further, it is possible to provide a graft kit including a length of graft on which the second stents may already be secured, and a plurality of first stents from which one or more may be selected for attachment to the graft. The selected stent or stents are then positioned on the graft, and chemically or mechanically secured to the graft prior to placement of the graft in the body passage. Such a kit would enable the physician to cut the graft to a desired length before securing the first stent to the end of the graft, thus allowing customization of the graft. As illustrated in FIG. 4, the second stents may be formed of a uniform width, and spaced equally from one another along the graft to provide a desired level of circumferential support to the inner and outer graft layers. Alternately, as shown in FIG. 5, the stents 14 may be formed of varying widths and may be spaced at irregular intervals along the graft, as necessary, to increase the flexibility of certain areas of the graft to enable the graft to be bent around curves in the passage.

Another feature of the graft kit is the ability to form radial holes in the graft where desired, permitting additional lengths of graft to be connected to the main graft to form a Y-shaped graft, presenting a main branch and side branches. Thus, the graft may be assembled in any desired configuration in order to accommodate placement within any desired body passage.

An installation apparatus used to support the graft during initial placement in the body passage is illustrated in FIG. 2.

and includes an elongated core 16 provided with a central axial passage, and a guide wire 18 received within the passage. The stents 12, 14 are wound onto the core prior to placement of the graft, and are retained in the contracted condition on the core by a sleeve 20. The sleeve represents a retaining means for retaining the stents in the contracted condition on the core 16 while the core is being inserted into the passage, and is shiftable relative to the core for releasing the stents to uncoil and move to their expanded conditions, with the first stent 12 bearing against the inner wall of the passage and the second stents 14 assuming their relaxed shape.

If desired, a flange may be provided on the core for retaining the first stent in place on the core while the sleeve is shifted. However, any other suitable means for allowing the sleeve to be removed from engagement with the first stent may be used.

A balloon 22 may be provided either on the installation apparatus or on a separate device, and is used for deforming the graft 10, when necessary, to the expanded condition so that the graft is expanded to the size of the second stents 14 and the desired diameter of the inner wall of the body passage. The balloon 22 may be inflated by conventional means to a diameter sufficient to deform the graft to the expanded diameter, shown in FIG. 7, in which the graft presents an outer diameter substantially equal to the inner wall of the passage. Although the balloon illustrated in FIG. 8 is long enough to extend between several of the stents, it may be constructed of a shorter length. However, when the balloon is shorter than the length of the graft, it is necessary to repeatedly inflate the balloon at different positions along the graft in order to deform the entire length thereof. In either case, the diameter of the balloon catheter is small enough to slide into the graft when the stents are in the contracted condition.

Figure 11:
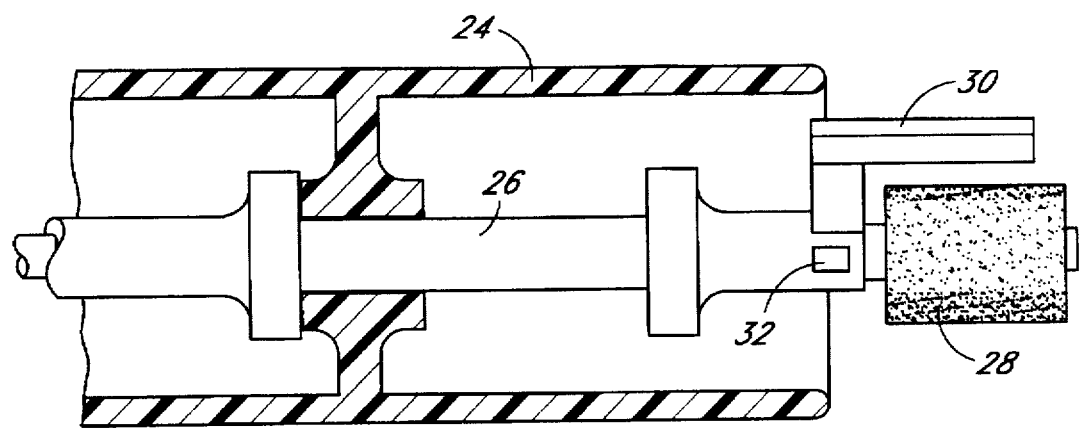
FIG. 11 is a sectional view of a removal device for use in removing the graft from the body passage.
Figure 12:
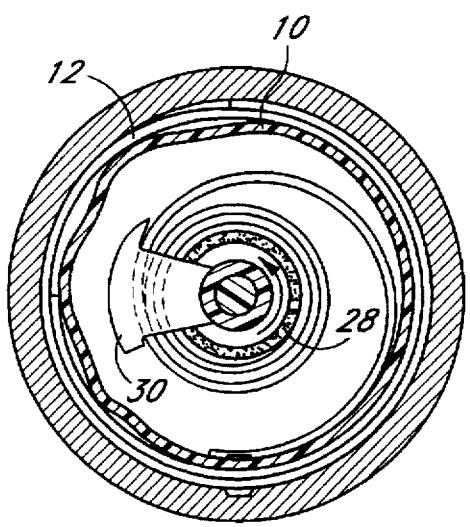
FIG. 12 is a cross-sectional view of the body passage, illustrating the use of the removal tool.

An apparatus for use in removing the graft from the body passage is illustrated in FIGS. 11 and 12, and includes a catheter sheath 24 presenting a shaft 26 that is axially shiftable and rotatable relative to the sheath. The shaft 26 supports a friction wheel 28 at the distal end thereof, the wheel being provided with an outer surface formed of a resilient material possessing a high coefficient of friction which enables the wheel to engage the inner layer of the first stent 12 so that the stent may be rewound to the contracted condition on the wheel as illustrated in FIG. 12. A flange 30 is provided on the shaft and extends over the wheel for urging the sheet toward the wheel as the flange and wheel rotate relative to the sheath. In addition, as shown in FIG. 11, an x-ray marker 32 is provided on the shaft of the wheel so that a physician manipulating the apparatus can determine its position within the passage from outside of the body.

The core 16 of the installation apparatus preferably includes a plurality of x-ray markers similar to the marker 32, which are longitudinally spaced a predetermined distance apart from one another so that the apparatus may be inserted into the passage to measure the dimensions of the damaged area before the graft is assembled. Alternately, a separate catheter provided with such measurement markers may be provided for use in combination with the installation apparatus. This measurement enables the physician to design and assemble a graft having the desired dimensions and configuration for use in the particular application.

As shown in FIG. 8, once the graft is assembled, it is mounted on the installation apparatus, with the stents 12, 14 wound onto the core 16 and retained in place by the sleeve 20. The installation apparatus is then inserted into the body passage and positioned at the damaged area of the passage. Thereafter, the sleeve 20 is shifted from engagement with the first stent so that the stent is allowed to unwind under the spring force present in the roll toward the expanded condition of the roll, which is shown in FIG. 3. The first stent 12 is sized to expand toward the relaxed condition in which the outer diameter is greater than the diameter of the inner wall of the passage. Thus, the stent engages the passage and retains the graft in position regardless of whether the inner wall of the passage expands or contracts over time.

Turning to FIG. 9, the graft assembly remains in the desired position while the sleeve releases the second stents 14, allowing them to move to the expanded, relaxed condition supporting the graft. Thereafter, if the graft is of the type illustrated in FIG. 6, the balloon is inflated by conventional means to a size which forces the graft to deform to an expanded condition, as shown in FIG. 7, having an outer diameter substantially equal to the diameter of the inner wall. As mentioned, if the balloon is shorter than the length of the graft, the balloon is moved along the graft and repeatedly inflated to deform each stent to the desired diameter.

Upon completion of the placement of the graft within the passage, the first stent 12 retains the graft in the desired position relative to the damaged section of the passage, and the second stents 14 support the graft along the length thereof. The graft 10 provides a barrier between the lumen of the body passage and the stents.

If it is necessary to remove the graft assembly, the removal apparatus is inserted into the passage and the shaft 26 is shifted axially relative to the sheath 24 so that the roller is uncovered and brought into alignment with the first stent 12. The flange 30 or another suitable means may be used to pierce the graft in order to engage the stent for winding on the wheel 28. Thereafter, as shown in FIG. 12, the shaft 26 is rotated so that the flange engages the inner layer of the stent and urges the layer toward the friction wheel. As the stent engages the wheel, it is gripped and wound around the wheel, moving back toward the contracted condition. Thus, the stent 12 is removed from engagement with the inner wall of the passage, and may be pulled from the passage upon removal of the apparatus. The stents 14 are deformed toward the contracted condition in the same manner as the stent 12 in order for the entire graft to be removed from the passage.

Returning to FIG. 9, once the installation tool has been removed from the body passage, and the graft assembly is properly positioned, it is preferred that a number of inner stents 34 be installed along the inner surface of the graft 10 in alignment with the first and second outer stents 12, 14. The purpose of these inner stents 34 is to hold the graft 10 against the inner circumferential surface of the outer stents and to prevent the graft from collapsing.

Each inner stent 34 is preferably formed of an initially flat flexible metal sheet arranged in a multiple layer roll having expanded and contracted conditions. The inner stents are preferably constructed of a stainless steel foil which is commercially available under the trade designation pH15-9 Condition CH900, having a thickness in an exemplary construction of 0.0127 millimeters. However, any other suitable material may be used.

The inner stents 34 are produced in the same manner as the first type of stent described above, and produce an inherent spring force which urges the inner stents toward the expanded condition. The expanded diameter of the stents 34 is designed to be slightly larger than the inner diameter of the installed outer stents 12, 14.

The inner stents 34 may be installed either by the same installation apparatus used to install the graft 10 and outer stents 12, 14, or by a separate installation catheter having a core on which the stents may be supported, a guide wire for guiding the catheter to the assembly, and a sleeve for retaining the stents on the core and releasing them at the desired axial location along the graft. As each inner stent is released from the installation apparatus, it expands against the graft 10, pressing the graft against the outer stent 12 or 14 at that position.

As shown in FIG. 10, once the inner stents 34 are installed, an inner graft 36 is positioned within the passage to cover the stents 34 and shield them from direct exposure to the lumen of the body passage. Although one long inner graft is illustrated in FIG. 10, several shorter, elongated grafts may be individually installed over each inner stent or over several of the inner stents. The inner graft is preferably positioned within the body passage in alignment with the outer graft 10, and is expanded so that it presses against the outer graft. Expansion of the inner graft may be achieved either by a balloon catheter, or by the pressure present in the body passage.

In order to hold the inner graft 36 in place on the assembly, an attachment means is provided for attaching the inner tubular graft to the outer graft 10. The attachment means may be chemical or mechanical, and preferably includes either an adhesive or a fastener employing hook and loop materials. Where a hook-and-loop fastener is used, either the hook or loop material is secured in a conventional fashion to the inner surface of the outer graft 10, while the other material is secured to the outer surface of the inner graft 36. By providing this construction, once the inner graft is positioned axially within the outer graft, the balloon 22 may be inflated to press the hook and loop materials together to secure the inner graft in place.

Although the present invention has been described with reference to the preferred embodiment illustrated in the attached drawing figures, it is noted that substitutions may be made and equivalents employed herein without departing from the scope of the invention as recited in the claims. For example, because the graft presents a completely closed lumen, open only at the ends, it is possible to employ the graft either intraluminally or as a bypass. When used as a bypass graft, each end of the graft is preferably provided with one of the first type of stent, and is independently placed into the passage on either side of the damaged area.

What is claimed is:

1. A graft assembly for placement in a body passage having a generally tubular inner wall of predetermined diameter, the graft assembly comprising:

an elongated tubular graft presenting inner and outer graft surfaces;

a first outer stent retained on said outer graft surface and having expanded and contracted conditions and possessing a spring force that urges the first outer stent toward the expanded condition, the first outer stent when in the expanded condition presenting an outer diameter greater than the predetermined diameter of the inner wall of the body passage;

a means for securing the first outer stent to the outer surface of the graft;

a second outer stent secured to the graft at a position longitudinally spaced from the first outer stent, the second outer stent having expanded and contracted conditions and possessing a spring force that urges the second outer stent toward the expanded condition, the second outer stent when in the expanded condition presenting an outer diameter smaller than the outer diameter of the first outer stent so that the second stent supports the graft at the position spaced from the first outer stent; and a means for securing the second outer stent to the outer surface of the graft; and a plurality of inner stents provided along the inner graft surface of the graft and sleeved within the first and second outer stents, each of the inner stents being movable between expanded and contracted conditions and possessing a spring force that urges the inner stent toward the expanded condition, the inner stents when in the expanded condition pressing the graft against the first and second outer stents.

2. A graft assembly as recited in claim 1, wherein the first outer stent includes a roll that, in the expanded condition, has at least two overlapping layers bearing against one another along substantially the entire circumference of the roll.

3. A graft assembly as recited in claim 2, wherein the roll is formed from a flexible sheet of stainless steel foil.

4. A graft assembly as recited in claim 1, wherein the means for securing the first outer stent to the graft includes a mechanical connection which provides a friction holding force of the graft when the first outer stent is in the expanded condition.

5. A graft assembly as recited in claim 1, wherein the means for securing the first stent to the graft includes an adhesive.

6. A graft assembly as recited in claim 1, wherein the second stent includes a roll that, in the expanded condition, has at least two overlapping layers which bear against one another along substantially the entire circumference of the roll.

7. A graft assembly as recited in claim 6, wherein the roll of the second stent is formed of metal.

8. A graft assembly as recited in claim 1, wherein a plurality of second outer stents are secured to the outer graft, and each second outer stent is spaced longitudinally from adjacent outer stents.

9. A graft assembly for placement in a body passage having a generally tubular inner wall of predetermined diameter, the graft assembly comprising:

an elongated outer tubular graft presenting inner and outer graft surfaces;

a first outer stent retained on said outer graft surface, the first outer stent having expanded and contracted conditions and possessing a spring force that urges the first outer stent toward the expanded condition, the first outer stent when in the expanded condition presenting an outer diameter greater than the predetermined diameter of the inner wall of the body passage;

a second outer stent secured to the graft at a position longitudinally spaced from the first outer stent, the second outer stent having expanded and contracted conditions and possessing a spring force that urges the second outer stent toward the expanded condition, the second outer stent when in the expanded condition presenting an outer diameter smaller than the outer diameter of the first outer stent so that the second stent supports the graft at the position spaced from the first outer stent;

a plurality of inner stents provided along the inner graft surface of the outer graft and sleeved within the first and second outer stents, each of the inner stents being movable between expanded and contracted conditions and possessing a spring force that urges the inner stent toward the expanded condition, the inner stents when in the expanded condition pressing the outer graft against the first and second outer stents; and at least one elongated inner tubular graft presenting inner and outer graft surfaces, and an attachment means for attaching the at least one inner tubular graft to the outer tubular graft with the at least one inner tubular graft covering the inner stents to shield the inner stents from direct exposure to the body passage.

10. A graft assembly as recited in claim 9, wherein the attachment means includes a mechanical fastener between the inner and outer grafts that is secured when the inner graft is pressed against the outer graft.

11. A graft assembly as recited in claim 10, wherein the fastner includes a hook material supported on one of the grafts and a loop material supported on the outer graft, wherein the material adhere to one another when the grafts are brought into mutual contact.

* * * * *